United States Patent [19]

Laki

[11] 4,423,076
[45] Dec. 27, 1983

[54] 1-BRANCHED-ALKYL-3-(2-HALOETHYL)-3-NITROSOUREAS AS NOVEL ANTITUMOR AGENTS

[75] Inventor: Koloman Laki, Bethesda, Md.

[73] Assignee: National Foundation for Cancer Research, Inc., Bethesda, Md.

[21] Appl. No.: 64,886

[22] Filed: Aug. 8, 1979

[51] Int. Cl.³ .................. C07C 127/15; A61K 31/17
[52] U.S. Cl. .................................. 424/322; 564/33
[58] Field of Search ............... 260/553 R; 424/322; 564/33

[56] References Cited

U.S. PATENT DOCUMENTS 4,039,578  8/1977  Suami ........................... 260/553 R
4,148,921  4/1979  Suami ........................ 260/553 R X
4,180,655  12/1979  Suami et al. ................ 260/553 R X

OTHER PUBLICATIONS

Montgomery et al., J. Med. Chem., 1977, vol. 20, No. 2, pp. 291–295.
Johnston et al., J. Med. Chem., 1966, vol. 9, No. 6, pp. 892–910.

Primary Examiner—Thomas A. Waltz
Attorney, Agent, or Firm—Fidelman, Wolffe & Waldron

[57] ABSTRACT

1-Branched-alkyl-3-(2-haloethyl)-3-nitrosoureas which exhibit antitumor activity. Pharamaceutical compositions containing these novel compounds and methods of using them are also disclosed.

13 Claims, No Drawings

1-BRANCHED-ALKYL-3-(2-HALOETHYL)-3-NITROSOUREAS AS NOVEL ANTITUMOR AGENTS

The present invention relates to novel nitrosourea derivatives useful for their antitumor activity. The invention also includes pharmaceutical compositions containing these compounds and methods of using them.

BACKGROUND OF THE INVENTION

In the past decade, the nitrosoureas have gained acceptance as potent antitumor agents (Johnston, et al., J. Med. Chem., 14:600 (1971)). The accepted mode of action appears to be through the release of isocyanate in vivo. The two compounds most frequently used clinically are 1-cyclohexyl-3-(-chloroethyl)-3-nitrosourea(CCNU) and 1,3-bis(2-chloroethyl)-1-nitrosourea(BCNU) which release in vivo an isocyanate derived from the unnitrosated side of the molecule, and an alkylating agent from the other side.

Numerous studies have been directed toward the metabolic products produced in vivo and in vitro in aqueous media, which consist of mainly 2-chloroethanol, vinyl chloride, acetaldehyde, and dichloroethane (Johnston, et al., J. Med. Chem., 18:634 (1975)). It is also known that the N-nitroso-N-alkyl ureido portion of the molecule alkylates DNA (deoxyribonucleic acid) in vivo and in vitro (Frei, et al., Biochem. J., 174:1031 (1978)). In fact, it has been shown that the carcinogenic effectiveness of agents such as N-methyl-N-nitrosourea correlate with the extent of alkylation of the guanine moiety in DNA of target tissues at the C-6 atom.

Alkylation of DNA occurs within an hour after administration of the nitrosourea, and the half-life of the alkylated products is about 24 to 48 hours ((Reed, et al., (Cancer Res., 35:568 (1975)). The study indicated that low doses of nitrosoureas pose only a small threat as mutagens, and hence, are not significantly carcinogenic. From this it may be postulated that the more transglutaminase-specific (see below) the isocyanate resulting from decomposition of the nitrosourea, the lower the required dose, resulting in a reduced risk of carcinogenesis from the antitumor agent.

It has recently been shown that a number of isocyanates are potent inhibitors of the enzyme transglutaminase (Gross, et al., J. Biol. Chem., 250:7693 (1975)), a calcium-dependent enzyme which catalyzes the lysine-glutamine crosslinking of certain proteins present on neoplastic cell surfaces. This enzyme has been implicated in the uncontrolled proliferation of cancer cells (Yancey and Laki, Ann. N.Y. Acad. Sci., 202:344 (1972)). It has been proposed that these crosslinked proteins form an extracellular coating causing the cell to be unrecognized by the cellular immune system, thus preventing normal destruction of foreign neoplastic tissue. The enzyme is fairly specific toward glutamine residues as substrates, and isocyanates resembling these residues have been found to be the most effective inhibitors (Gross, et al., J. Biol. Chem., 250:7693 (1975)).

The structure of the active site of the transglutaminase has been found to contain the pentapeptide sequence —Tyr—Gly—Gln—Cys—Trp— and has the shape of a pocket approximately 5×5 Angstroms (Folk and Cole, J. Biol. Chem., 241:3238 (1966)).

BRIEF DESCRIPTION OF THE INVENTION

According to the hypothesis upon which the invention is based, a superior inhibitor of transglutaminase would have, in view of the sequence and size indicated above, hydrophobic moieties directed away from, but in proximity to, the pocket at the active site. Two possible inhibitors meeting these criteria are neopentyl isocyanate (I) and neohexyl isocyanate (II) which can be seen to resemble glutamine (III) in size:

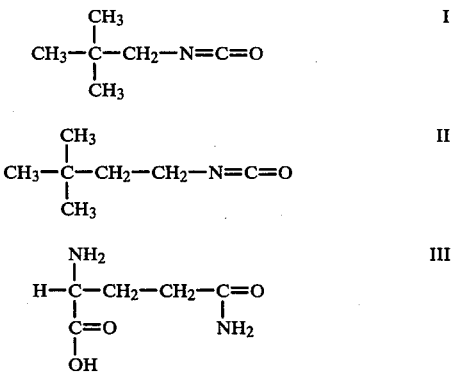

The hypotesis of the invention is supported by the fact that tert-butyl groups, or other hydrophobic groups, attached to the beta- or gamma-carbon of glutamic acid produce superior substrates for transglutaminase (Gross and Folk, J. Biol. Chem., 248:130 (1973)). Ester analogs of these compounds are also substrates (Gross and Folk, J. Biol. Chem., 249:3021 (1974)).

It has been shown that isocyanates inhibit the transglutaminase through alkyl thiocarbamate ester formation through the single active site sulfhydryl group (Gross, et al., J. Biol. Chem., 250:7693 (1975)):

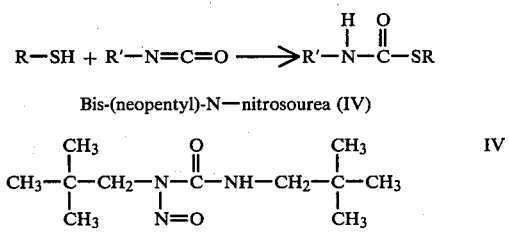

was synthesized as a compound which would release neopentyl isocyanate (I) in vivo resulting in inhibition of transglutaminase. However, the limited solubility of this compound prevented its clinical evaluation.

Recent studies have shown that the activity of nitrosoureas is markedly enhanced by the presence of the 2-chloroethyl group on the nitrosated side of the compound (Montgomery, Cancer Treat. Rep., 60:651 (1976); Johnston, et al., J. Med. Chem., 9:892 (1966); Farmer, et al., J. Med. Chem., 21:514 (1978)). Since the 2-chloroethyl group also enhances solubility, it became the group of choice at the 3-position in this study.

The following compounds of the invention were synthesized as described in the Experimental section:

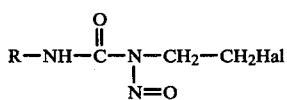

| | | |
|---|---|---|
| V, | R = | Neopentyl |
| VI, | R = | Neohexyl |
| VII, | R = | Isopentyl |
| VIII, | R = | Isobutyl |
| | Hal = | Cl or F |

Chemical studies revealed that the neopentyl and neohexyl isocyanates are remarkably stable in water-acetone (1:3) at 57° C. without substantial amounts being hydrolyzed even after a three-day period at pH 6.0. Both have half-lives of greater than 30 minutes at physiological pH and temperature.

Thus, the branched alkyl groups of the compounds of the invention were selected using the criterion that they should be substrates for, and thus be selective inhibitors of, transglutaminase. As noted above, the work of Montgomery discloses a single 1-branched-alkyl-3-(2-chloroethyl)-3-nitrosourea, namely 1-(1-methyl-hexyl)-3-(2-chloroethyl)-3-nitrosourea (IX):

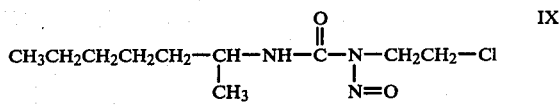

While this compound is a 1-branched-alkyl-3-(2-chloroethyl)-3-nitrosourea, it does not fulfill the steric criteria outlined above for optimal inhibitory activity.

It is not desired to limit the invention by the theoretical considerations presented herein, and the above discussion is included merely for purposes of background discussion.

OBJECTS OF THE INVENTION

It is an object of the present invention to provide novel compounds having antitumor activity.

It is another object of the invention to provide novel compounds which inhibit the activity of transglutaminase.

Still another object of the present invention is to provide novel compounds which are effective antitumor agents at low doses so as to minimize adverse mutagenic and/or carcinogenic effects.

An additional object of the invention is to provide compositions containing the novel compounds and methods of using them.

EXPERIMENTAL SECTION

Melting points were determined using a Thomas Hoover capillary melting point apparatus and are uncorrected. Infrared (IR) spectra were obtained using a Perkin Elmer 397 spectrophotometer, and NMR (nuclear magnetic resonance) spectra were taken on a Bruker WP80DS system with tetramethylsilane as an internal standard. Elemental analyses were carried out by Galbraith Laboratories, Knoxville, Tenn. Tert-Butyl acetyl chloride and 3,3-dimethyl-1-butanol were obtained from Aldrich Chemical Co. and were used without further purification as a result of satisfactory NMR analysis.

1-Neopentyl-3-(2-Chloroethyl) Urea.

Neopentylamine (8.7 g, 0.1 mol) was dissolved in 50 ml of anhydrous diethyl ether and cooled to 5° C. 2-Chloroethyl isocyanate (10.5 g, 0.1 mol) dissolved in an additional 50 ml of ether was added over 30 minutes while maintaining a temperature of less than 10° C. Stirring continued for an additional hour, and the cold mixture was filtered and washed with chilled ether. The compound was dried in a desiccator over sodium hydroxide overnight giving 15.4 g (80%) as a white powder, MP (melting point) 90°-1° C. (decomposes). Elemental analysis showed the following:

| | Calculated | Found |
|---|---|---|
| Carbon | 49.97% | 49.87% |
| Hydrogen | 8.87% | 8.89% |
| Nitrogen | 14.52% | 14.54% |
| Chlorine | 18.47% | 18.40% |

IR analysis showed bands at 1630/cm (C=O) and 1535/cm (N—C=O). NMR showed a singlet (9H) at 0.8 ppm and a multiplet (6H) at 3.4 ppm.

1-Neopentyl-3-(2-Chloroethyl)-3-Nitrosourea (V).

The entire yield of 1-neopentyl-3-(2-chloroethyl) urea (0.08 mol) was dissolved in 120 ml of concentrated HCl:ethanol, 2:1 at 5° C. in a 500 ml round bottom flask equipped with magnetic stirring. Sodium nitrite (5.5 g, 0.08 mol) was dissolved in 30 ml of water and added to the solution over a ten-minute period. Stirring continued for 2 hrs, and the yellow, crystalline precipitate was filtered and washed with five 100 ml portions of chilled distilled water. The product was dried in vacuo for 18 hrs. giving 15 g (84%) which melted with decomposition at 52°-3° C. IR analysis showed peaks at 1730/cm (C=O) and 1520/cm (C—N—H). NMR showed a singlet (9H) at 1 ppm, a doublet (2H, J=6.5 HZ) at 3.3 ppm, a triplet (2H, J=6.5 Hz) at 3.6 ppm, and a triplet (2H, J=6.5 Hz) at 4.2 ppm.

1-Neohexyl-3-(2-Chloroethyl) Urea.

A 5 g quantity of 3,3-dimethyl butylamine (0.5 mol) was dissolved in 30 ml of anhydrous diethyl ether and stirred on an ice bath. 2-Chloroethyl isocyanate (5.25 g, 0.5 mol) dissolved in 15 ml of ether was added maintaining a temperature of 10° C. or less, and stirring continued for 2 hrs. Filtering the product and washing with four 5 ml portions of chilled ether afforded 6.2 g (60%) which melted at 84° C. (decomposes). IR analysis showed peaks at 1625/cm (C=O) and 1580/cm (N—C=O). NMR: singlet (9H) at 0.9 ppm, multiplet (2H) at 1.3 ppm, multiplet (2H) at 3.2 ppm, multiplet (4H) at 3.5 ppm, singlet (1H) at 5.5 ppm, and singlet (1H) at 5.7 ppm.

1-Neohexyl-3-(2-Chloroethyl)-3-Nitrosourea (VI).

A 2.07 g (10 mmol) quantity of 1-neohexyl-3-(2-chloroethyl) urea was dissolved in 15 ml of concentrated HCl:ethanol, 2:1, at 10° C., and 690 mg (10 mmol) sodium nitrite dissolved in 3 ml of water was added. Stirring at 5° C. continued for 1.5 hrs. and the precipitate was washed with four 25 ml portions of distilled water. After drying in vacuo overnight, 1.7 g (74%) of the product was obtained which melted at 43.0°-43.5° C. (decomposes). IR analysis showed peaks at 1705/cm (C=O) and 1525/cm (C—N=O). NMR: singlet (9H) at 0.9 ppm, multiplet (2H) at 1.3 ppm, symmetrical multiplet (6H) at 3.8 ppm. No evidence of isomeric material was detected.

1-Isopentyl-3-(2-Chloroethyl) Urea.

Isopentylamine (8.7 g, 0.1 mol) was dissolved in 100 ml of anhydrous ether and cooled to less than 10° C. 2-Chloroethyl isocyanate (10.5 g, 0.1 mol) was dissolved in 20 ml of ether and added to the rapidly stirring reaction mixture at less than 10° C. Stirring continued 1 hr. longer and the preciptiate was filtered and washed with four 20 ml portions of chilled ether. After drying in vacuo overnight, 16.5 g (85%) of product obtained as a white powder, MP 58°-9° C. IR analysis showed peaks at 1620/cm (C=O) and 1575/cm (N—C=O). NMR showed a doublet (6H, J=7 Hz) at 0.9 ppm, a triplet (2H, J=7 Hz) at 1.4 ppm, a multiplet (1H) at 1.8 ppm, a multiplet (1H) at 3.2 ppm, a multiplet (4H) at 3.6 ppm, a singlet (1H) at 5.7 ppm, and a singlet (1H) at 6.0 ppm.

1-Isopentyl-3-(2-Chloroethyl)-3-Nitrosourea (VII).

A 1.92 g (10 mmol) quantity of 1-isopentyl-3-(2-chloroethyl) urea was dissolved in 15 ml of HCl:ethanol, 2:1, and cooled to 5° C. Sodium nitrite (690 mg, 10 mmol) dissolved in 3 ml of water was added in portions with stirring, after which stirring was continued for an additional 2 hrs. The mixture was filtered and 50 ml of water was added. Extracting with two 20 ml portions of ethyl acetate followed by evaporation of the solvent afforded the product as an oil which did not solidify on standing. Similar results were obtained using 98% formic acid as the solvent. IR analysis showed peaks at 1705/cm (C=O) and 1525/cm (N—C=O). NMR analysis showed a doublet (6H, J=7 Hz) at 0.9 ppm, a triplet (2H, J=7 Hz) at 1.4 ppm, a multiplet (1H) at 1.8 ppm, a multiplet (6H) at 3.8 ppm, and a singlet (1H) at 7.4 ppm.

1-Isobutyl-3-(2-Chloroethyl) Urea.

Isobutylamine (7.3 g, 0.1 mol) was dissolved in 20 ml of diethyl ether and cooled to less than 5° C. Chloroethyl isocyanate (10.5 g, 0.1 mol) dissolved in 15 ml of ether was added maintaining a temperature between 0° and 5° C. with vigorous stirring. Stirring continued an additional 2 hrs. the mixture was cooled to −5° C., and the product (4.1 g, 46%) was filtered and dried in vacuo for 18 hrs. over KOH, MP 79.5° C. (decomposes). IR analysis showed peaks at 1630/cm (C=O) and 1585/cm (N—C=O). NMR: Doublet at 0.9 ppm (J=6.4 Hz), multiplet (1H) at 2.1 ppm, quartet (2H) at 2.9 ppm (J=6.4 Hz), multiplet (4H) at 3.5 ppm.

1-Isobutyl-3-(2-Chloroethyl)-3-Nitrosourea (VIII).

A 2 g (11.2 mmol) quantity of 1-isobutyl-3-(2-chloroethyl) urea was dissolved in 25 ml of concentrated HCl:ethanol, 2:1, and cooled to 5° C. A solution of 773 mg (11.2 mmol) of sodium nitrite in 5 ml of water was added in portions and the mixture was stirred at this temperature for 2 hrs. The crystalline yellow solid was filtered and dried in vacuo overnight giving 1.6 g (70%) of the product, MP 51° C. (decomposes). IR analysis showed peaks at 1705/cm (C=O) and 1525/cm (C—N=O). NMR: Doublet (6H, J=6.8 Hz) at 0.9 ppm, multiplet (1H) at 2.0 ppm, multiplet (6H) at 3.7 ppm.

1-Branched-alkyl-3-(2-fluoroethyl)-3-nitrosoureas.

Syntheses corresponding to those described above may be performed using the 2-fluoroethyl compounds to produce the 1-branched-alkyl-3-(2-fluoroethyl)-3-nitrosoureas.

CLINICAL STUDIES

Experiment I

A single dose of 1-neopentyl-3-(2-chloroethyl)-3-nitrosourea (NCNU) was injected intraperitoneally (ip) in CDF1 mice which had been implanted ip two days earlier with approximately $10 \times 10^5$ murine leukemia L1210 tumor cells. The NCNU was dissolved in emulphor EL-620 (polyoxyethylated; GAF Corporation, New York, N.Y.) and raised to the desired volume with 0.85% sodium chloride. The increase in median lifespan (ILS) of the test animals above control (untreated) animals is presented in Table I.

TABLE I

Effects of Single-Dose Treatment with NCNU Against Two-Day Murine Leukemia L1210

| Dose (mg/kg) | % ILS |
| --- | --- |
| 100 | 275 +* |
| 75 | 275 + |
| 50 | 100 |
| 25 | 37.5 |

*The plus sign indicates that the animals have not yet all died and the experiments are continuing.

Experiment II

The study of Experiment I was conducted using approximately $5 \times 10^5$ murine leukemia P388 tumor cells (0.1 ml of a 1:100 dilution). Results are presented in Table II.

TABLE II

Effects of Single-Dose Treatment with NCNU Against Two-Day Murine Leukemia P388

| Dose (mg/mouse) | % ILS |
| --- | --- |
| 2.0 | 483 +* |
| 1.0 | 91.7 |
| 0.5 | 41.5 |

*The plus sign indicates that the animals have not yet all died and the experiments are continuing.

Experiment III

The effect of NCNU was tested against Yancey's lymphocytic leukemia (YLL) which had been implanted subcutaneously (sc) two days before injection of the drug. The single injection of 0.1 ml of a solution of one spleen of a YLL bearing mouse homogenized in 10 ml Locke's Solution was given either intraperitoneally or subcutaneously. Table III presents the increase in median life span of test animals over control animals.

TABLE III

Effects of Single-Dose Treatment with NCNU Against Two-Day Yancey's Lymphocytic Leukemia

| Dose | | Route of Injection | % ILS |
| --- | --- | --- | --- |
| 2.0 | mg/mouse | ip | 264 +* |
| 1.0 | mg/mouse | ip | 64.3 |
| 0.5 | mg/mouse | ip | 14.3 |
| 25 | mg/kg | ip | 13.3 |
| 50 | mg/kg | ip | 60.0 |
| 75 | mg/kg | ip | 66.6 |
| 2.0 | mg/mouse | sc | 78.0 |
| 1.0 | mg/mouse | sc | 64.3 |
| 0.5 | mg/mouse | sc | 35.7 |
| 25 | mg/kg | sc | 6.6 |
| 50 | mg/kg | sc | 60.0 |
| 75 | mg/kg | sc | 73.3 |
| 1.0 | mg/mouse | ip | 33.3 |
| 0.5 | mg/mouse | ip | 6.7 |
| 1.0 | mg/mouse | sc | 20.0 |
| 0.5 | mg/mouse | sc | 13.3 |

*The plus sign indicates that the animals have not yet all died and the experiments are continuing.

Experiment IV

The study of Experiment III was conducted with NCNU treatment beginning at 2 or 7 days after implantation of YLL tumors. NCNU injection was ip or sc on a schedule of one time per week for 4 weeks, twice per week for 4 weeks, or a single dose. Results are provided in Table IV.

TABLE IV

Effects of NCNU Against Yancey's Lymphocytic Leukemia

| Dose | Day After Implantation Treatment Was Begun | Route of Injection | Injection Schedule | % ILS |
|---|---|---|---|---|
| 1.0 mg/mouse | 7 | ip | once | 66.6 |
| 0.5 mg/mouse | 7 | ip | once | 6.7 |
| 1.0 mg/mouse | 7 | sc | once | 66.6 |
| 0.5 mg/mouse | 7 | sc | once | 6.7 |
| 2.0 mg/mouse | 2 | ip | 1x/wk for 4 wks | 14.3 |
| 1.0 mg/mouse | 2 | ip | 1x/wk for 4 wks | 178.6 |
| 0.5 mg/mouse | 2 | ip | 1x/wk for 4 wks | 28.6 |
| 75 mg/kg | 2 | ip | 1x/wk for 4 wks | 100 +* |
| 50 mg/kg | 2 | ip | 1x/wk for 4 wks | 100 + |
| 25 mg/kg | 2 | ip | 1x/wk for 4 wks | 100 + |
| 2.0 mg/mouse | 2 | sc | 1x/wk for 4 wks | 264 + |
| 1.0 mg/mouse | 2 | sc | 1x/wk for 4 wks | 207.1 + |
| 0.5 mg/mouse | 2 | sc | 1x/wk for 4 wks | 114.3 + |
| 75 mg/kg | 2 | sc | 1x/wk for 4 wks | 100 + |
| 50 mg/kg | 2 | sc | 1x/wk for 4 wks | 100 + |
| 25 mg/kg | 2 | sc | 1x/wk for 4 wks | 100 + |
| 75 mg/kg | 2 | ip | 2x/wk for 4 wks | 66.6 |
| 50 mg/kg | 2 | ip | 2x/wk for 4 wks | 100 + |
| 25 mg/kg | 2 | ip | 2x/wk for 4 wks | 100 + |
| 75 mg/kg | 2 | sc | 2x/wk for 4 wks | 0 |
| 50 mg/kg | 2 | sc | 2x/wk for 4 wks | 100 + |
| 25 mg/kg | 2 | sc | 2x/wk for 4 wks | 100 + |

*The plus sign indicates that the animals have not yet all died and the experiments are continuing.

Experiment V

Toxicity studies were conducted by injecting a single dose of NCNU ip. Survival data is set forth in Table V.

TABLE V

Toxicity of NCNU in CDF1 Normal Mice

| Dose | Deaths (%) |
|---|---|
| 1.0 mg/mouse | 0 |
| 2.0 mg/mouse | 60 at day 13, others survived |
| 4.0 mg/mouse | 100 at day 10 |
| 8.0 mg/mouse | 100 at day 8 |
| 16.0 mg/mouse | 100 at day 4 |
| 20.0 mg/mouse | 100 at day 1 |
| 32.0 mg/mouse | 100 at day 1 |
| 100 mg/kg | 100 at day 13 |
| 150 mg/kg | 100 at day 11 |
| 200 mg/kg | 100 at day 9 |
| 225 mg/kg | 100 at day 9 |
| 250 mg/kg | 100 at day 8 |
| 500 mg/kg | 100 at day 5 |
| 750 mg/kg | 100 at day 2 |
| 1000 mg/kg | 100 at day 1 |

PHARMACEUTICAL COMPOSITIONS

The compounds of this invention can be employed in useful pharmaceutical compositions in such dosage forms as tablets, capsules, powder packets, liquid solutions, suspensions or elixirs for oral administration; liquid for parenteral use, and in certain cases, suspensions for parenteral use. In such compositions, the active ingredient will ordinarily be present in an amount of at least 0.5% by weight based on the total weight of the composition and not more than 95% by weight.

Besides the active ingredient compound of this invention, the antitumore composition can contain a solid or liquid non-toxic pharamaceutical carrier for the active ingredient.

The capsules, tablets, and powders will generally constitute from about 1 to about 95% and preferably from about 5 to 90% by weight of active ingredient. These dosage forms preferably contain from about 5 milligrams to about 500 milligrams of active ingredient, with about 7 milligrams to about 250 milligrams most preferred.

The pharmaceutical carrier can be a sterile liquid such as water, or a suitable oil, including those of petroleum, animal, or vegetable oil of synthetic origin, for example, peanut oil, soybean oil, mineral oil, sesame oil, and the like. In general, water, saline, aqueous dextrose (glucose), and related sugar solutions and glycols such as propylene glycol and polyethylene glycols are preferred liquid carriers, particularly for injectible solutions. Sterile injectible solutions will ordinarily contain from about 0.5 to about 25% and preferably about 1 to about 10% by weight of the active ingredient.

Oral administration can be in a suitable suspension or syrup, in which the active ingredient ordinarily will constitute from about 0.7 to about 10% and preferably about 1 to about 5% by weight. The pharmaceutical carrier in the composition can be an aqueous vehicle such as an aromatic water, a syrup, or a pharmaceutical mucilage.

Suitable pharmaceutical carriers are described in "Remington's Pharmaceutical Sciences" by E. W. Martin, a well-known reference text in this field.

The following examples will further illustrate the preparation of pharmaceutical compositions of the invention.

EXAMPLE A

A large number of unit capsules are prepared by filling standard two-piece hard gelatin capsules each with 250 milligrams of powdered 1-neopentyl-3-(2-chloroethyl)-3-nitrosourea, 110 milligrams of lactose, 32 milligrams of talc, and 8 milligrams stearate.

EXAMPLE B

A mixture of 1-neopentyl-3-(2-fluoroethyl)-3-nitrosourea in soybean oil is prepared and injected by means of a positive displacement pump into gelatin to form soft gelatin capsules containing 35 milligrams of the active ingredient. The capsules are washed in petroleum ether and dried.

EXAMPLE C

A large number of tablets are prepared by conventional procedures so that the dosage unit is 100 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatabilty or delay absorption.

EXAMPLE D

A parenteral composition suitable for administration by injection is prepared by stirring 1.5% by weight of 1-isopentyl-3-(2-chloroethyl)-3-nitrosourea in 10% by volume propylene glycol and water. The solution is sterilized by filtration.

EXAMPLE E

An aqueous suspension is prepared for oral administration so that each 5 millilters contain 50 milligrams of finely divided 1-neohexyl-3-(2-chloroethyl)-3-nitrosourea, 500 milligrams of acacia, 5 milligrams of sodium benzoate, 1.0 grams of sorbitol solution, U.S.P., 5 milligrams of sodium saccharin, and 0.025 milliliters of vanilla tincture.

EXAMPLE F

A parenteral composition suitable for administration by injection is prepared by dissolving 1% by weight of 1-neopentyl-3-(2-chloroethyl)-3-nitrosourea in sodium chloride injection U.S.P. XV and adjusting the pH of the solution to between 6 and 7. The solution is sterilized by filtration.

A wide variety of compositions included within the invention can be prepared by substituting other compounds embraced by this invention for the specific compounds named in Examples A-F above and substituting other suitable pharmaceutical carriers described in "Remington's Pharmaceutical Sciences".

The compounds of this invention can be administered in the treatment of any of the various forms of cancer by any means that effects contact of the active ingredient compound with the site of action in the body of a warm-blooded animal. For example, administration can be parenteral, i.e., subcutaneous, intravenous, intramuscular, or intraperitoneal; alternatively or concurrently, administration can be by the oral route.

For the purpose of this disclosure, a warm-blooded animal is a member of the animal kingdom possessed of a homeostatic mechanism and includes mammals and birds.

The dosage administered is dependent on the age, health, and weight of the recipient, the extent of disease, kind of concurrent treatment, frequency of treatment and the effect desired. Usually, a daily dosage of active ingredient compound can be from about 0.1 to 150 milligrams per kilogram of body weight. Ordinarily, from 2.0 to 75, and preferably 10 to 50 milligrams per day administered in one or more doses daily is effective to obtain the desired results.

HUMAN STUDIES

Patients having advanced stages of various forms of cancer are treated by subcutaneous injection of two 25 mg/kg doses of NCNU in water or by intravenous administration of 1 milligram NCNU/ml 0.9% saline to provide a total daily dose of 50 mg/kg; a full clinical examination is carried out prior to and after administration. Tumor growth is measured where possible by palpition, X-rays and photography.

Following treatment patients show marked clinical improvement within several days. Inflammation gradually subsides and tumor size frequently decreases.

The following types of cancer in addition to others, may be treated with compounds of the invention: (1) undifferentiated carcinoma of the (R) kidney with metastases, (2) adenocarcinoma of the colon with liver metastases, (3) intraduct carcinoma of the breast (stage IV) with bone metastases, (4) recurrent melanoma, (5) adenocarinoma of the breast with brain metastases and (6) squamous cell carcinoma of the lung.

The above clinical studies establish that the α-branched-alkyl-3-(2-haloethyl)-3-nitrosourea compounds of the invention are useful in the treatment of various forms of cancer. Continuous intravenous administration inhibits tumor activity and frequently leads to a general remission of the disease.

The mode of action of the compounds of the invention is, at this point, unclear. However the empirical observation that cells stop proliferation when exposed to these compounds is sufficient to warrant their use in the treatment of such serious, heretofore untreatable, and often fatal diseases, such as cancer.

We claim:

1. A compound of the formula

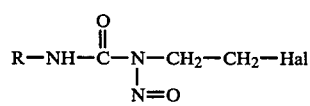

wherein Hal is selected from the group consisting of fluorine and chlorine and wherein R is selected from the group consisting of neopentyl, neohexyl, isopentyl and isobutyl.

2. A compound of claim 1, wherein Hal is fluorine.
3. A compound of claim 1, wherein Hal is chlorine.
4. A compound of claim 2, wherein R is neopentyl.
5. A compound of claim 3, wherein R is neopentyl.
6. A compound of claim 2, wherein R is neohexyl.
7. A compound of claim 3, wherein R is neohexyl.
8. A compound of claim 2, wherein R is isopentyl.
9. A compound of claim 3, wherein R is isopentyl.
10. A compound of claim 2, wherein R is isobutyl.
11. A compound of claim 3, wherein R is isobutyl.
12. A method of inhibiting tumor growth comprising administering to humans or animals an effective amount of a compound of claim 1.
13. A composition for inhibiting the growth of tumors in humans and animals, comprising an effective tumor-inhibiting amount of a compound of claim 1 and a pharmaceutical carrier therefor.

* * * * *